United States Patent [19]

Hydes et al.

[11] 4,230,631
[45] Oct. 28, 1980

[54] PLATINUM COORDINATION COMPOUNDS

[75] Inventors: Paul C. Hydes; Bernard W. Malerbi, both of Reading, England

[73] Assignee: Johnson, Matthey & Co., Limited, London, England

[21] Appl. No.: 952,213

[22] Filed: Oct. 17, 1978

[30] Foreign Application Priority Data

Oct. 19, 1977 [GB] United Kingdom ............... 43492/77
May 18, 1978 [GB] United Kingdom ............... 20461/78

[51] Int. Cl.² ............................................. C07F 15/00
[52] U.S. Cl. ................................. 260/429 R; 424/287
[58] Field of Search .................................... 260/429 R

[56] References Cited
U.S. PATENT DOCUMENTS

| | | | |
|---|---|---|---|
| 3,892,790 | 7/1975 | Tobe et al. | 260/429 R |
| 3,904,663 | 9/1975 | Tobe et al. | 260/429 R |
| 4,115,418 | 9/1978 | Gale et al. | 260/429 R |

OTHER PUBLICATIONS

Cleare et al., Bioinorganic Chemistry 2, pp. 187-199 (1973).
Leh et al., J. of Pharmaceutical Sciences 65 (3), pp. 315-325 (1976).

Primary Examiner—Helen M. S. Sneed
Attorney, Agent, or Firm—Cushman, Darby & Cushman

[57] ABSTRACT

A cis co-ordination compound of platinum having the structure

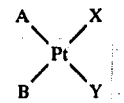

in which X and Y are the same or different ligands selected from sulphate, phosphate, nitrate, carboxylate, halogen-substituted carboxylate and water and A and B are the same or different branched chain aliphatic amines co-ordinated to the Pt through their N atoms, such that the platinum is present as $Pt^{2+}$.

5 Claims, No Drawings

PLATINUM COORDINATION COMPOUNDS

This invention relates to new platinum co-ordination compounds and to pharmaceutical compositions containing them.

According to a first aspect of the present invention, a composition of matter comprises a cis co-ordination compound of platinum having the structure

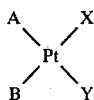

in which X and Y are the same or different ligands selected from sulphate, phosphate, nitrate, carboxylate, substituted carboxylate and water and A and B are the same or different branched chain aliphatic amines co-ordinated to the Pt through their N atoms, such that the platinum is present as $Pt^{2+}$. By phosphate, we mean both $H_2PO_4^-$ and $HPO_4^{2-}$.

Where X and/or Y is represented by carboxylate or substituted carboxylate, the general formula of which is $C_nR_{2n+1}CO_2H$, we prefer that n is an integer from 1 to 9 inclusive and the R groups are the same or different and are selected from hydrogen, substituted or unsubstituted straight- or branched-chain alkyl, aryl, alkaryl, aralkyl, alkenyl, cycloalkyl and cycloalkenyl halogen, pseudohalogen (as hereinafter defined), hydroxy, carbonyl, formyl, nitro, amido, amino, alkoxy, aryloxy and sulphonic acid salts. We intend the above definition also to include oxygen and sulphur, such that one doubly-bonded oxygen or sulphur atom is represented by two H groups and/or Y may also be a dicarboxylate, e.g. an oxalate, tartronate, phthalate, sulphate or tartrate.

Where X and Y are both carboxylate, they can together comprise a dicarboxylate bidentate ligand, for example oxalate and ligands having the general formula

where $n^1$ is an integer from 2 to 6, $R^1$ and $R^2$ are the same or different and are selected from H, lower alkyl, aryl, alkaryl, aralkyl, alkenyl, cycloalkyl, cycloalkenyl, alkoxy, aryloxy, halogen pseudohalogen, OH, or are combined with the carbon atoms to form a cycloalkyl, cycloalkenyl or an aryl group, and substituted derivatives thereof, and y and z are either 0 or 1 as long as (y+z) is equal to 1 or 2.

Suitable dicarboxylate ligands are the succinato, glutarato (pentanedioato), adipato (hexanedioato), pimelato (heptanedioato), malato (cis-butenedioato) and phthalato (o-benzenedicarboxylate) ligands and these may be either substituted or unsubstituted.

The ligands may contain substituents selected from the group consisting of lower alkyl, (e.g. methyl, ethyl, n-propyl, isopropyl, n-butyl); aryl, (e.g. phenyl, lower alkyl-, lower alkenyl-, halo-, nitro-, lower alkoxy-substituted phenyl and naphthyl); aralkyl, (e.g., phenyl-methyl (benzyl), Z-(1-naphthyl) methyl); alkenyl, (e.g. 4-amino-1-butene, allyl); cyclo-alkyl, (e.g., cyclopropyl, cyclohexyl); cyclo-alkenyl, (e.g. Z-cyclopenten-1-yl), 2-cyclo-hexen-1-yl); alkoxy; (e.g. methoxy, ethoxy); and hydroxy.

The branched chain aliphatic amine has the general formula:

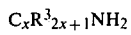

in which n is an integer from 3 to 9 inclusive and that the $R^3$ groups are the same or different and are selected from hydrogen, substituted or unsubstituted alkyl, aryl, alkaryl, aralkyl, alkenyl, cycloalkyl and cycloalkenyl halogen, pseudohalogen, hydroxy, carbonyl, formyl, nitro, amido, amino, acylamino, sulphonic acid, sulphonic acid salt, carboxylic acid ester and carboxylic acid salt. Even more preferably all the $R^3$ groups are hydrogen. However, where one or more of the $R^3$ groups is other than hydrogen, it can be a lower alkyl, for example methyl or ethyl, or a solubilizing group, for example a sulphonic acid, carboxylic acid, carboxylic acid salt or a sulphonic acid salt. Where a solubilizing group is used in the form of a salt, the salt can be for example, the sodium, potassium or lithium salt, where conditions are appropriate and the clinical conditions require high solubility. We intend the above definition of $R^3$ also to include oxygen and sulphur, such that one doubly-bonded oxygen or sulphur atom is represented by two $R^3$ groups.

Examples of particular compounds according to the invention are the bis(isopropylamine) are bis (isopentylamine) complexes of platinum (II) with phthalate, oxalate, sulphate, carbonylate, tartrate, pyruvate and gluconate ligands.

The term "pseudohalogen" in this specification has the meaning given on p. 560 of "Advanced Inorganic Chemistry" by Cotton and Wilkinson, Interscience Publishers, 1966, as being "a molecule consisting of more than two electronegative atoms which, in the free state, resembles the halogens; these pseudohalogens give rise to anions which resemble the halide ions in behaviour". Examples of suitable pseudohalogenides are cyanide, cyanate, thiocyanate and azide.

The term "cis" as applied to the compounds of the invention indicates that the compounds have planar structure and that A cannot be in a position trans to B and that X cannot be in a position trans to Y.

Normally the compound is used in association with a pharmaceutically acceptable carrier therefor. Accordingly, in a second aspect, the present invention provides a pharmaceutical composition which comprises a compound according to the first aspect of the invention and a pharmaceutically-acceptable carrier for said compound; these compositions can be formulated so as to be suitable, for example, for parenteral or oral administration to animals.

PREPARATION OF PLATINUM COMPLEXES

The following preparative details and results are quoted by way of examples of the preparation of certain specific complexes according to the invention. Throughout the Examples, reference to the "aquo complex" means the complex containing a mixture of aquo and hydroxo species prepared according to the reaction

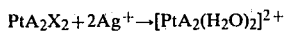

EXAMPLE 1

Aquabis(iso-pentylamine)sulphatoplatinum II)-[Pt(SO_4)(C_5R_{11}NH_2)_2(H_2O)]

cis-[PtI_2A_2] (30 g, 0.048 Mole) was suspended in water (150 ml) and stirred until a smooth slurry was obtained. To this slurry was added silver nitrate (16.35 g) dissolved in water (30 ml). After the mixture had been stirred for 0.5 hours at 40° C. it was thoroughly triturated using a glass rod with a flattened end. Stirring and heating was continued with thorough trituration at 2 and 4 hour intervals. After a total reaction time of 5 hours the mixture was filtered through a porosity 4 filter and the solids washed twice on the filter by trituration with fresh portions of water. The combined filtrate and washings were stirred with charcoal and re-filtered through a porosity 4 filter. The clear filtrate was treated with a warm saturated solution of sodium sulphate (ca. 20 g in 40 ml water). An immediate white precipitate of the product formed, but the mixture was stirred for 1 hour at 50° C. to ensure complete coordination of the sulphate. The product was filtered off on a porosity 3 filter and washed on the filter using water and then acetone. It was dried overnight at 50° C. in vacuo.

The crude product was recrystallised from a hot 1:1 mixture of ethanol and water. Recovery of the pure complex was low as it appeared to react with the solvents.

| Elemental analysis: | C | H | O | N | S |
|---|---|---|---|---|---|
| Calculated % | 24.83 | 5.83 | 16.55 | 5.79 | 6.62 |
| Found % | 25.43 | 5.80 | 15.39 | 5.68 | 6.17 |

The unrecrystallised material, which typically contains 7.0–7.2% S, fits the theoretical figures quite well if ca. 2% $Na_2SO_4$ is assumed to be present.

EXAMPLE 2

Preparation of sulphate and phosphate complexes of bis(isopropylamine)platinum(II)

These complexes had previously been prepared in a crude form by addition of sodium sulphate and disodium hydrogenphosphate to $[Pt(i-C_3H_7NH_2)_2(H_2O)_2](NO_3)_2$ to give white solids on stirring at 50° C. for three hours. The preparations were repeated and the infra-red spectre of the two sets of products were found to be identical, confirming the reproducibility of this method. However, recrystallisation by dissolution in hot water and addition of the free acid or its sodium salt was unsuccessful and the products were shown to be impure or incorrectly formulated by the elemental assays below.

| $[Pt(SO_4) (i-C_3H_7NH_2)_2(H_2O)]$ | | | | | |
|---|---|---|---|---|---|
| | Et | C | H | N | O | S |
| Calculated % | 45.68 | 16.86 | 4.68 | 6.56 | 18.73 | 7.49 |
| Found % | | 17.10 | 4.98 | 6.89 | 19.03 | 7.12 |
| $Pt(HPO_4) (i-C_3N_7NH_2)_2(H_2O)]$ | | | | | |
| | Pt | C | H | N | O | S |
| Calculated % | 45.68 | 16.86 | 4.92 | 6.56 | 18.73 | 7.26 |
| Found % | | 17.26 | 4.76 | 7.66 | 16.88 | 5.69 |

Consequently the only method of preparation likely to be successful is the reaction of "the aquo complex" with $Ag_2SO_4$, $Ag_2HPO_4$ and evaporation of the solution to dryness over sulphuric acid in vacuo as for the nitrate and chloroacetate complexes (see Examples 3 and 4 below).

EXAMPLE 3

Preparation of $[Pt(ClCH_2CO_2)_2(i-C_3H_7NH_2)_2]$

Addition of sodium chloroacetate at pH 5.5 to the aquo complex gave a white precipitate. However, this complex was recrystallised from hot dilute chloroacetic acid in very low yield to give colourless cubic crystals. The elemental analysis of this sample (A) was poor, therefore the complex was dissolved in water, filtered through charcoal, and again evaporated to dryness over concentrated sulphuric acid in vacuo (sample (B)).

| Elemental analysis: | It | C | H | N | O | Cl |
|---|---|---|---|---|---|---|
| Calculated % | 39.01 | 24.00 | 4.40 | 5.60 | 12.80 | 14.20 |
| Found (A) | | 23.46 | 4.54 | 5.98 | 13.50 | 13.55 |
| (B) | | 23.73 | 4.50 | 5.72 | 13.41 | 13.95 |

EXAMPLE 4

Preparation of $[Pt(NO_3)_2(i-C_3H_7NH_2)_2]$

The aquo solution was evaporated to dryness twice over sulphuric acid in vacuo, to give pale yellow granular crystals.

| Elemental analysis: | Pt | C | H | N | O |
|---|---|---|---|---|---|
| Calculated % | 44.64 | 16.47 | 4.12 | 12.81 | 21.96 |
| Found % | | 16.39 | 4.20 | 12.75 | 22.29 |

Evaporation of the aquo solution to dryness on a water bath resulted in a viscous red mass. The red impurity was efficiently leached out with acetone and water washing of the residue resulted in a cream coloured powder with an infra-red spectrum identical to the above crystals.

EXAMPLE 5 cis-bis (isopentylamine) bis (chloroacetato) platinum (II)-$[Pt(C_2H_2O_2Cl)_2(C_5H_{11}NH_2)_2]$ $[PtI_2A_2]$ (40 g, 0.065 mole) was triturated with water (200 ml) and stirred with thorough trituration at hourly intervals with silver nitrate (21.9 g, 0.129 mole) at 40°–50° C. for 4 hours to form the diaquo complex. The solution thus obtained, after confirming that $Ag^+$ was absent, was mixed with a solution of potassium chloroacetate, which had been prepared by neutralising chloroacetic acid with KOH to pH 6–7. No visible sign of reaction could be seen at first but the solution soon became turbid and resulted in a sticky oil which eventually solidified on standing. After decanting the supernatant aqueous solution, the residue was set aside to dry and subsequently dissolved in warm ethanol (60° C.). On standing at room temperature, the ethanolic solution deposited white crystals of the chloroacetato complex.

| Elemental analysis: | C | H | O | N | Cl |
|---|---|---|---|---|---|
| Calculated % | 36.19 | 5.42 | 11.50 | 5.03 | 12.76 |
| Found % | 28.67 | 5.18 | 13.49 | 5.65 | 11.55 |

This complex is difficult to prepare in a state of adequate purity.

EXAMPLE 6

Aquabis (isopentylamine) phosphatoplatinum (II) $[Pt(HPO_4)(C_5H_{11}NH_2)_2(H_2O)]$ cis-$[PtI_2A_2]$ (40 g, 0.065 mole) was converted to the diaquo species and this solution was allowed to react with an almost saturated solution of $Na_2HPO_4$(20 g, 0.141 mole). The product separated almost immediately as a fine white precipitate, but the mixture was stirred for 2 hours at 50° C. to ensure coordination of the phosphate. After washing with water and acetone the product was vacuum dried.

Yield 11.0 g (37%).

Attempts at recrystallisation from hot water, ethanol, DMF and 1:1 ethanol water were unsuccessful, owing to insufficient solubility. Therefore two separate batches of crude material were submitted for analysis.

| Elemental analysis: | C | H | O | N | P |
|---|---|---|---|---|---|
| Found(I)% | 23.10 | 6.00 | 18.22 | 5.64 | 6.10 |
| Found (II)% | 23.57 | 6.23 | 18.40 | 5.77 | 5.83 |
| Calculated for Pt A2NH O4 2H2O % | 23.94 | 6.22 | 19.15 | 5.59 | 6.18 |

For unrecrystallised material these results show fairly good agreement and indicate that the complex contains 1 molecule of water of hydration in addition to 1 co-ordinated water molecule.

EXAMPLE 7

Bis (isobutylamine)oxalatoplatinum(II), [Pt(C$_2$O$_4$)(i-C$_4$H$_9$NH$_2$)$_2$]

A solution of the isobutylamine aquo complex (37 ml, 0.024 mol) was added to a warm stirred solution of potassium oxalate (13 g, monohydrate, 0.07 mol) in 40 ml of water. The white precipitate so formed was stirred for 30 minutes, filtered off on a porosity 4 sinter, washed with water and dried in vacuo at 50° C.

The crude oxalato complex was recrystallised as follows. The product was added to a stirred, vigorously boiling aqueous solution of 0.1 M potassium oxalate (800 ml). The solution was boiled for 30 minutes to effect dissolution during which time the solution darkened owing to some platinum formation. The solution was then treated with charcoal, stirred, cooled to 80° C. and filtered through a porosity 4 sinter. White crystals formed on cooling the filtrate to 25° C. and after storage for 3 days at 5° C., the product was filtered off, washed with water and air dried.

Yield=0.5 g (5%).

The low yield is due to instability of the product in boiling 0.1 M potassium oxalate.

| Elemental Analysis | Pt | C | H | N | O |
|---|---|---|---|---|---|
| Calculated % | 45.4 | 28.0 | 5.2 | 6.5 | 14.9 |
| Found % | — | 28.1 | 5.4 | 6.6 | — |

Infra-red Spectrum

The nitrogen-hydrogen stretching modes ($v_{N-H}$) occur at 3110 and 3140 cm$^{-1}$ and there is an absorption at 1673 cm$^{-1}$ due to the carbonyl stretching vibration ($v_{c=0}$) of the oxalate ligand.

EXAMPLE 8

Cis-bis (isobutylamine) bis(chloroacetato) platinum (II), cis-[Pt(ClCH$_2$CO$_2$)$_2$(i-C$_4$H$_9$NH$_2$)$_2$]

A solution of potassium chloroacetate in 100 mls of water, prepared from chloroacetic acid (21.6 g, 0.14 mol) was added to a solution of the isobutylamine aquo complex in water (76 mls, 0.046 mol). A blue solution was formed immediately in which a dark blue-green oil settled. A white suspension was also observed. The mixture was allowed to stand for 60 hours and then the solids were filtered off on a porosity 3 sinter, washed well with water and air dried. The solid was then crushed in a mortar, washed with diethyl ether and dried in vacuo at 60° C. The crude produce was pale green.

Crude yield=9.6 g (40%).

The crude produce (9.6 g) was dissolved in 50–60 mls of hot ethanol. The orange solution was stirred with charcoal and filtered while hot through a porosity 4 sinter. White acicular crystals formed on cooling the filtrate which was subsequently chilled at 5° C. overnight. The crystals filtered off on a porosity 3 sinter and washed twice with ethanol, causing them to effloresce to a white powder, which was dried in vacuo at 40° C.

Yield-5 g (overall yield=21%).

| Elemental analysis | Pt | C | H | N | O | Cl |
|---|---|---|---|---|---|---|
| Calculated % | 36.9 | 27.3 | 5.0 | 5.3 | 12.1 | 13.4 |
| Found % | — | 27.2 | 5.1 | 5.3 | — | — |

Infra-red spectrum

The nitrogen-hydrogen stretching modes ($v$N—H) occur at 3230 and 3160 cm$^{-1}$ and there are chloroacetate absorptions at 1670 and 1645 cm$^{-1}$ ($v$C=O).

EXAMPLE 9

Aquobis (isobutylamine)sulphatoplatinum(II) cis-[Pt(SO$_4$)(H$_2$O)(i-C$_4$H$_9$NH$_2$)$_2$]

Concentrated sulphuric acid (24 mls, 0.45 mol) was added slowly to a chilled (0° C.) stirred solution of the isobutylamine aquo complex (76 mls, 0.046 mol) ensuring that the temperature did not exceed 30° C. The solution was stirred for 1 hour during which time some white crystals formed. The product was filtered off on a porosity 3 sinter, washed well with water and dried in vacuo.

Yield=7 g (33%).

The complex was analysed without further purification.

| Elemental analysis | Pt | C | H | N | O | S |
|---|---|---|---|---|---|---|
| Calculated % | 42.8 | 21.1 | 5.3 | 6.2 | 17.6 | 7.0 |
| Found % | — | 21.0 | 5.4 | 6.3 | — | — |

Infra-red spectrum

The nitrogen-hydrogen stretching modes ($v$N—H) occur at 3210 and 3140 cm$^{-1}$, there are sulphate absorptions at 1180, 1123, 1050 and 1028 cm$^{-1}$; and water absorptions occur at 1600 cm$^{-1}$ with a very broad shoulder around 3500 cm$^{-1}$.

EXAMPLE 10

Oxalatobis(isopropylamine)platinum(II)-[Pt(C$_2$O$_4$)(i-C$_3$H$_7$NH$_2$)$_2$]

cis-[PtI$_2$(i-C$_3$H$_7$NH$_2$)$_2$](67.8 g, 0.120 mole) was slurried with a vigorously stirred solution of silver nitrate (38.6 g, 0.227 mole) in water (150 ml). The mixture was stirred for 4 hours at 40°–50° C., and then with charcoal at 25° C. before being filtered through a porosity 4 sinter to give a pale yellow solution. The filter was washed once with about 30 ml of water directly into the filtrate which was found to be silver free on testing with NaCl.

The total volume of solution was 180 ml. Theoretical yield of cis-[bis(isopropylamine)diaquo Pt(II)]$^{++}$ in solution was 0.114 mole. The aquo complex (120 ml, 0.075 mole) was added to a warm stirred solution of potassium oxalate (72 g, 0.39 mole) giving an immediate white precipitate, but stirring continued for 0.5 hours. The precipitate was then filtered off on a porosity 3 sinter, washed well with water and dried in vacuo at 60° C.

Crude yield=20.6 g (45%).

Recrystallisation

The crude produce (12 g) was added to a vigorously boiling and stirred solution of potassium oxalate (27 g) in water (1450 ml) to give a clear solution, which was treated with charcoal, cooled to 80° C. and filtered through a preheated porosity 4 sinter. On cooling to room temperature white needles appeared. The mixture was kept at 5° C. overnight and then the product filtered on a porosity 3 sinter, washed with water, air dried and then dried in vacuo at 60° C.

Yield of recrystallised produce=7.8 g, (65% recovery on recrystallisation, overall yield 29.3%).

| Assay: | Pt | C | H | N | O |
|---|---|---|---|---|---|
| Calculated % | 48.6 | 23.9 | 4.5 | 7.0 | 16.0 |
| Found % | — | 24.3 | 4.5 | 7.2 | |

Infra-red spectrum

The nitrogen-hydrogen stretching modes ($\nu$n-H) occur at 3190 and 3120 cm$^{-1}$ and there are oxalate absorptions at 1690 and 1640 cm$^{-1}$ (broad) ($\nu$C=O).

EXAMPLE 11

Cis-bis(bromoacetato)bis(isopropylamine)platinum(II)

A solution of potassium bromoacetate (0.15 mole) [prepared from bromoacetic acid (20.4 g) and potassium hydroxide (8.2 g)] in 100 ml water adjusted to pH 6 was added to a well stirred aqueous solution of the Pt(II) bis(isopropylamine) aquo complex (0.05 mole in 60 ml) at 25°-30° C. Within a few minutes of mixing the solutions a white oily solid began to separate. The mixture was stirred for 1 hour and left to stand overnight. On standing the oil had solidified, was filtered off and washed thoroughly with water. It was then covered with ether and kept at 0° C. overnight. The solid was then filtered off and dried at 60° C. in vacuo.

Crude yield 11.9 g (41%) 1 g of the product was recrystallised from ethanol giving 50% recovery.

| Elemental Analysis: | Pt | C | H | N | O | Br |
|---|---|---|---|---|---|---|
| Calculated % | 33.1 | 20.4 | 3.8 | 4.8 | 10.9 | 27.1 |
| Found % | — | 20.6 | 3.9 | 4.7 | 10.7 | — |

Clinical Testing Data

Complexes according to the invention were tested for antitumour activity against L-1210 leukaemia in mice. In the results which follow, dosages are quoted in mg/Kg body weight and the evaluation of effectiveness (% T/C) is calculated as the median survival time of treated mice divided by the median survival time of untreated (control) mice expressed as a percentage. Thus a % T/C of 100 indicates no activity and a % T/C of greater than or equal to 125 is considered to be indicative of significant antitumour activity.

| | |
|---|---|
| (i) Bis(chloroacetato)bis(iso-propylamine)platinum(II) | |
| Single dose @ 32 mg/Kg | % T/C = 179 |
| Daily dose for 9 days @ 16 mg/Kg | % T/C = 207 |
| (ii) Dinitrobis(iso-propylamine)platinum(II) | |
| Single dose @ 64 mg/Kg | % T/C = 171 |
| Daily dose for 9 days @ 16 mg/Kg | % T/C = 193 |
| (iii) Aquo bis(isopropylamine sulphatoplatinum(II) | |
| Single dose @ 22.6 mg/kg | % T/C = 150 |
| Daily dose for 9 days @ 5.7 mg/Kg | % T/C = 167 |
| @ 11 mg/Kg | % T/C = 167 |
| (iv) Bis(chloroacetato)bis(iso-butylamine)platinum(II) | |
| Single dose @ 52 mg/Kg | % T/C = 150 |
| Daily dose for 9 days @ 26 mg/Kg | % T/C = 150 |
| (v) Aquobis(isobutylamine)sulphatoplatinum (II) | |
| Single dose @ 15 mg/Kg | % T/C = 150 |
| Daily dose for 9 days @ 7.5 mg/Kg | % T/C = 129 |

We claim:

1. A cis co-ordination compound of platinum having the structure

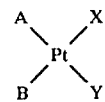

in which X and Y are the same or different ligands selected from sulphate, phosphate, nitrate, haloacetate and water or together comprise oxalato, succinato, glutarato, adipato, pimelato, malato or phthalato ligands and A and B are selected from the group consisting of isopropylamine, isobutylamine and isopentylamine coordinated to the Pt through their N atoms, such that the platinum is present as Pt$^{2+}$.

2. A compound according to claim 1 wherein the phosphate is in the form of H$_2$PO$_4^-$ or HPO$_4^{2-}$.

3. A compound according to claim 1 selected from the group consisting of:
Pt(SO$_4$)(iso-C$_5$H$_{11}$NH$_2$)$_2$(H$_2$O);
Pt(SO$_4$)(iso-C$_3$H$_7$NH$_2$)$_2$(H$_2$O);
Pt(HPO$_4$)(iso-C$_3$H$_7$NH$_2$)$_2$(H$_2$O);
Pt(ClCH$_2$CO$_2$)$_2$(iso-C$_3$H$_7$NH$_2$)$_2$;
Pt(NO$_3$)$_2$(iso-C$_3$H$_7$NH$_2$)$_2$;
Pt(C$_2$H$_2$O$_2$Cl)$_2$(iso-C$_5$H$_{11}$NH$_2$)$_2$;
Pt(HPO$_4$)(iso-C$_5$H$_{11}$NH$_2$)$_2$(H$_2$O);
Pt(C$_2$O$_4$)(iso-C$_4$H$_9$NH$_2$)$_2$;
cis-Pt(ClCH$_2$CO$_2$)$_2$(iso-C$_4$H$_9$NH$_2$)$_2$;
cis-Pt(SO$_4$)(H$_2$O)(iso-C$_4$H$_9$NH$_2$)$_2$;
Pt(C$_2$O$_4$)(iso-C$_3$H$_7$NH$_2$)$_2$; and
cis-Pt(BrCH$_2$CO$_2$)$_2$(iso-C$_3$H$_7$NH$_2$)$_2$.

4. A cis co-ordination compound of platinum according to claim 1 wherein X and Y together comprise a dicarboxylate bidentate ligand selected from succinato, glutarato, adipato, pimelato, malato and phthalato ligands.

5. A compound according to claim 1 wherein X and Y are chloroaceto and A and B are both isopropylamine.

* * * * *